US005576220A

United States Patent [19]
Hudson et al.

[11] Patent Number: 5,576,220
[45] Date of Patent: Nov. 19, 1996

[54] THIN FILM HPMP MATRIX SYSTEMS AND METHODS FOR CONSTRUCTING AND DISPLAYING LIGANDS

[75] Inventors: Derek Hudson, San Anselmo; Charles R. Johnson, Berkeley; Michael J. Ross, Hillsborough; Kevin R. Shoemaker, San Francisco; Robert T. Cass, San Mateo; Lutz B. Giebel, Burlingame, all of Calif.

[73] Assignee: Arris Pharmaceutical Corporation, South San Francisco, Calif.

[21] Appl. No.: 19,725

[22] Filed: Feb. 19, 1993

[51] Int. Cl.$^6$ .................................................. G01N 33/543
[52] U.S. Cl. ......................... 436/518; 436/528; 436/529; 436/530; 436/531; 436/807
[58] Field of Search ..................................... 436/518, 528, 436/529, 530, 531, 807; 424/422, 426, 484, 488; 428/309.4; 435/6, 7.1

[56] References Cited

U.S. PATENT DOCUMENTS

| 4,822,681 | 4/1989 | Schossler et al. | 428/405 |
| 5,077,210 | 12/1991 | Eigler et al. | 435/176 |
| 5,188,733 | 2/1993 | Wang et al. | 210/321.84 |

FOREIGN PATENT DOCUMENTS

| 9005305 | 5/1990 | WIPO . |
| 9005295 | 9/1990 | WIPO . |
| 91/13098 | 9/1991 | WIPO . |
| 9206380 | 9/1992 | WIPO . |
| 92/21976 | 12/1992 | WIPO . |

OTHER PUBLICATIONS

Lofas et al., Sensors and Actuators B, 5, pp. 79–84 (1991) "Bioanalysis with surface plasmon resonance".
Birnbaum et al., Current Opinion in Biotechnology, 3, pp. 49–54 (1992) "Peptide Screenining".
Lam, K. S. et al., "The selectide process: Rapid generation of large synthetic peptide libraries linked to identification and structure determination of acceptor–binding ligands"; *Peptides, Chemistry and Biology Proceedings of the Twelfth American Peptide Symposium;* pp. 492–495, 1992.
Hughes, J. et al., "Identification of two related pentapeptides from the brain with potent opiate agonist activity", *Nature*, vol. 258, No. 5536, pp. 577–579, Dec. 18, 1975.
Lofas, S. and Johnsson, B. A Novel Hydrogel Matrix on Gold Surfaces in Surface Plasmon Resonance Sensors for Fast and Efficient Covalent Immobilization of Ligands, J. Chem. Soc., Chem. Commun., 1990, pp. 1526–1528.

*Primary Examiner*—Lora M. Green
*Attorney, Agent, or Firm*—Oblon, Spivak, McClelland, Maier & Neustadt, P.C.

[57] ABSTRACT

The invention relates to methods and systems of unhindered construction and display of tethered organic ligand molecules, and more particularly to preparation and use of thin film, substantially non-crosslinked hydrophilic polar multifunctionalized polymers (HPMPs) anchored to a variety of functionalized substrates so that the HPMP forms a thin film matrix layer providing a unique highly hydrated, high dielectric environment equivalent to an aqueous solution, for affinity binding of Ligands (L) to Tagged Target Molecules (TTMs). Ligands, and especially $MER_n$ ligand libraries such as peptide libraries, are singly tethered to the HPMP by a "permanent" strong covalent bond so that subsequent displacement of the TTM does not also displace the ligand from the HPMP, thereby making the HPMP tethered Ligand library reusable. The HPMP thin film is on the order of 200–2000 Å thick, is highly accessible (to the TTMs), and permits flexible, 3-D display of the singly tethered ligands for free permeability therein of the TTMs for affinity binding. The 3-D nature of the HPMP film provides high amplification of display, and the open nature of the matrix permits rapid elution of excess TTMs and other molecules. Importantly, the HPMP matrix layer, while providing amplification is also non-masking, being essentially transparent to detection methods. The combination of the reuseability, amplification and non-masking properties results in a very significant, many-fold increase in sensitivity and speed of screening assays.

15 Claims, 6 Drawing Sheets

MASKED BIFUNCTIONAL DEXTRAN

A | NaOH

AMINO MASKED CARBOXYL DEXTRAN

B
1. EDC, NHS (STEP E, FIG. 2)
   AMINO FUNCTIONALIZED SURFACE
2. TFA

FIG. 3

END PRODUCT
TETHER LOADED DEXTRAN WINK

Fig. 6 UPTAKE OF LABELED STREPTAVIDIN BY HPQ LOADED DEXTRAN HPMP STAPLED TO WINKS

THIN FILM HPMP MATRIX SYSTEMS AND METHODS FOR CONSTRUCTING AND DISPLAYING LIGANDS

CROSS REFERENCE TO RELATED APPLICATION

This application is related to co-pending, commonly-owned application Ser. No. 07/939,065 filed Sep. 2, 1992, entitled PEPTIDE IDENTIFICATION OF LEADS AND OPTIMIZATION TECHNOLOGY (herein PILOT), the disclosure of which is hereby incorporated by reference. That application covers novel methods and apparatus systems for preparation and use of ASBCL's, Addressable Synthetic Biopolymer Combinatorial Libraries. This application is directed to novel hydrophilic polar multi-functionalized polymer (HPMP) matrix systems for construction and display of bioactive ligands in an aqueous environment, which HPMP matrices may be used, inter alia, in connection with the PILOT support surface systems employed in that prior application.

FIELD

This application relates to compositions and methods for synthesis and use of novel thin film hydrophilic molecular matrices for construction and display of ligands, especially bioactive molecules. More particularly, the invention relates to the use of thin film matrices of hydrophilic polar multi-functionalized polymers, such as carboxymethyl cellulose (CMC) or dextran, to which may be selectively attached and later ligated, a wide variety of ligands, organic and inorganic compounds of biochemical interest, for identification of the affinity and/or biochemical activity of the ligands with respect to selected tagged target molecules (TTMs), and for affinity purification or separation of TTMs from biochemical cocktails. By way of example of an important principal embodiment, the invention is directed to CMC or dextran matrix layers and their methods of preparation and use as environmental layers which are selectively chemically bonded (anchored) to a variety of substrates, and upon which selected organic molecules and mixtures thereof (ligands) may be assembled from synthons by known chemical processes, or pre-prepared and covalently bonded thereto, e.g., combinatorical libraries assembled from AAs, nucleotides, mono- or bicyclic ring compounds, sugars or the like, for display to determine their affinity to a variety of TTM's for a variety of purposes, e.g., purification, screening, amplification, isolation and the like.

BACKGROUND

In modern molecular biology and pharmacology, it has been found that a variety of factors are involved in producing a specific biological response. On the molecular level receptor-mediated cellular processes, and binding of effector molecules may result from combinations of hydrophobic, aromatic, charge transfer, salt bridging and hydrogen bonding interactions. For productive binding to occur it is vital that these forces and the groups which mediate them be displayed in appropriate conformations. A bioactive molecule may have agonist or antagonist activity, and may be a vital component of therapeutically useful compounds. Activity involves, inter alia, the several interactions mentioned of a biologically active molecule, a ligand, to a target molecule. An example is where a small ligand effectively blocks a larger ligand from binding to its target molecule, a natural biological receptor, e.g., to prevent the target from having an adverse effect on a tissue or organism. Conversely, a ligand may "turn on" a target molecule to engage in or initiate activity e.g., biochemical signal transduction.

These structure activity relationships are complex 3-D puzzles complicated by the in situ environment and the nature of the respective substituent groups of the ligand and target. The target and ligand molecules in fact are somewhat flexible, inter alia because of the manner in which the constituent atoms thereof bond to themselves and other molecules. For example, the flexure may be due in part to hydrogen bonding of different degrees of strength at different places along the molecules, and to the rotation around covalent bonds in the ligand molecule. Further, the isoelectric strength of the medium and the environment of the molecules plays a very important role. Steric hindrance by surfaces upon which small molecules are displayed may totally mask significant binding observable in solution. Display in proximity to surfaces, or within gel type polymers, will be similarly effected by the effective dielectric constant, changing the magnitude of all binding forces, and grossly affecting conformation, and therefore the "fit" between molecules.

Additionally, there are a wide range of degrees of affinity "fit" between ligand and target, and likewise between target and receptors, ranging from partial to complete fit. There is a concomitant range of effectiveness of a ligand to bind to target molecules, and thereby trigger a natural receptor, block, or ameliorate the adverse biological effects of the target on natural receptors, or inhibit the activity of an enzyme.

Another aspect of the problem is the vast numbers of potential candidate ligands considering the enormous number of molecular, isomeric and polymeric formulas. These numbers are increased by orders of magnitude when considering the variety of steric configurations and range of flexure. For example, considering the screening of hexapeptide ligands for biological blocking affinity of target molecules, there are some 64 million hexapeptides constructable from all the combinations of the 20 D-amino acids, an equal number for the 20 L-amino acids, and an even greater number for non-natural amino acids. Where the ligands are longer, the molecules have a greater chance of adopting a number of different conformations and thereby result in presentation of a number of different possible affinity combinations.

The two commonly used approaches rely either on solution interactions of the library ligand with a target, or supporting the ligand on a solid phase. The advantages of a supported library over solution interaction is the ability to rapidly identify ligands by content addressability, or to sequence the ligand or a surrogate tag for the ligand after identification. In contrast, deconvolution of soluble libraries only allows identification of concensus ligands, but not individual ligands.

Accordingly, there have been created various sized "libraries" of related organic molecules, i.e., a pre-selected set of ligand variations, on different types of solid supports. A variety of methods are known for producing such solid-phase supported libraries of organic molecules (ligands) as an aid in drug discovery. These include the Selectide one peptide per bead approach, the Affymax photolithographic approach, and the Arris PILOT addressable array approaches. The PILOT approach is the subject of co-pending Ser. No. 07/939,065, and the Selectide and Affymax approaches are summarized in the background thereof.

A major problem of potential library methods, is how to "display" the combinatorial ligand constituents, the concept of the term "display" including holding the ligand on or securing it to the substrate. Many ligand molecules have very low solubility in aqueous media, which is the usual solvent or carrier for target molecules flowed thereover during affinity screening. If the ligands are displayed on glass, silicon or polystyrene surfaces, for example, they can interact strongly with the surface on which they are displayed, introducing an artifact into the screening process. With the Affymax procedure, the bulk effect of the rigid silica matrix not only restricts the synthetic efficiency, but also introduces steric hindrance barriers to access by the target acceptor molecules.

Access to displayed ligands by target molecules is critical for success of the screening process. These target molecules are often large proteins or nucleotides which cannot easily diffuse into cross-linked gels.

It is particularly noteworthy that the Selectide process uses cross-linked polyacrylamide and polystyrene particles which permit reasonably efficient syntheses, but the cross-linking prevents access of biological target acceptors to any other than the surface molecules.

Accordingly, there is a need for a minimally sterically hindered system and method for the assembly and/or display of ligands for identification of binding constituents of target molecules that does not introduce unnatural steric artifacts or hindrances, yet is amenable to rapid, addressable screening techniques, the goal being highly sensitive biospecific ligand/target molecule interaction screening, purification, isolation, recovery and analysis.

THE INVENTION

OBJECTS

Its an object of this invention to provide a hydrophilic, polar multi-functionalized polymer (HPMP) capable of forming an open, flexible, non-gel, essentially non-crosslinked 3-D matrix layer which is selectibly anchorable to a substrate surface, and serves as a "framework" for singly tethering preselected libraries of $MER_n$ ligands, and provides a highly accessible, flexible, 3-D display for free permeability of TTM's for highly sensitive, amplified affinity binding.

It is another object of the invention to provide methods for preparation, attachment and use of such HPMP layers to a variety of substrates, preferably the polymer discs of the PILOT addressable array systems.

It is another object of this invention to provide systems and methods for amplifying displays of $MER_n$ ligands for affinity binding of TTM's.

It is another object of this invention to provide thin matrix film ligand display systems to permit rapid diffusion of unbound molecules from the matrix back into the bulk solvent.

It is another object of this invention to provide a ligand display system and method of identifying bound targets, which system provides improved selectivity and sensitivity.

It is another object of this invention to provide systems and methods for displaying ligands for affinity binding of targets under natural, hydrated conditions, and which permits rapid elution of excess target and other molecules.

It is another object of the invention to provide a non-masking, freely permeable, open, 3-D matrix layer providing a hydrated, high dielectric environment substantially equivalent to a natural aqueous solution for affinity binding of singly and permanently tethered ligands to displaceable TTM's, which layer can be selectively anchored to a wide variety of substrates, with the anchoring being tuneable by adjusting the anchor loading, and methods of preparation of the layer and use thereof.

It is a further object of this invention to provide HPMP's attached to surfaces suitable for the assembly of biomolecules from sub-units or synthons, so that the ensemble is stable to all synthesis and deprotection conditions.

Still other objects will be evident from the specification, drawings and claims.

SUMMARY

The invention relates to methods and systems of non-sterically hindered display of organic molecules, and more particularly to preparation and use of substantially non-crosslinked hydrophilic polar multi-functionalized polymers (HPMPs) anchored to a variety of functionalized substrates so that the HPMP forms a thin film non-masking layer providing a unique environment substantially equivalent to an aqueous solution, for affinity binding of ligands (L) to Tagged Target Molecules (TTMs). Ligands, and especially $MER_n$ ligand libraries, are singly tethered to the HPMP by a "permanent" strong covalent bond so that subsequent displacement of the TTM does not also displace the ligand from the HPMP.

The HPMP layer environment is a high accessible (to the TTMs), flexible, 3-D display of the singly tethered ligands providing free permeability therein of the TTMs for affinity binding. The 3-D nature of the HPMP layer provides a highly efficient interaction, between Ls and TTMs, and thereby enhanced binding. Compared to flat surface support-bound display methods, the 3-D matrix of this invention permits a larger number of $MER_n$s to be displayed for a given surface area, providing effective amplification of the assay signals.

Unlike cross-linked thick gels, the open nature of the HPMP matrix and its limited thin film depth permits rapid elution of excess unbound TTMs and other molecules. The matrix results in a highly hydrated, high dielectric environment similar to an aqueous solution. Importantly, the HPMP matrix layer, while providing amplification, is also non-masking, i.e., it is essentially transparent to detection methods. The combination of the amplification and non-masking properties results in a very significant, many-fold increase in sensitivity of screening assays.

The displayed organic molecules and mixtures thereof, herein broadly called ligands, include but are not limited to, libraries assembled from synthons, such as AA's, nucleotides, mono or bicyclic ring compounds, sugars, most functionalizable organic moieties, and combinations thereof. Other examples of the use of the system includes use with biotin, antihistamines, benzodiazapines, and the like, which bind biological receptors. The availability of libraries of such diverse materials displayed on the system of this invention will significantly expedite discovery of new drugs.

The matrices and methods of the invention are more specifically useful for optimal identification of a binding constituent to any particular biologically relevant protein, but may also be useful in a variety of diagnostic and therapeutic applications. For example, the system may be used for drug delivery. A drug may be tethered by a cleavable linker to an HPMP matrix-coated implant surface, and then under the effect of an endogenous enzyme which acts on the linker, the drug is slowly released, resulting in controlled drug delivery over a long time period.

The system and method of this invention is compatible with a wide range of organic molecules. It not only facilitates their assembly, but also presents them in an essentially 100% aqueous environment, and displays them so that the biological acceptor molecule interacts with them efficiently. It is a particular merit of this invention that the nature of the molecular matrix cuts down interactions between individual displayed ligand molecules. This minimization of environmental effects results in better synthetic efficiencies during assembly of ligands from synthons than prior art systems.

The invention involves the addition of covalently-modified long chain polysaccharides, such as CMC or dextran, to functionalized substrate surfaces. The substrate (SU) may be any bio-compatible, functionalizable or pre-functionalized material capable of covalent bonding to spacer arm anchor molecules. Examples of such substrates include solid substrates (monolithic blocks), membranes, films, laminates, spherical and irregular particles, and woven or non-woven filtration materials prepared, for example, from polyolefins, such as polyethylene, polypropylene, halogenated polyolefins (such as PVDF, PVC etc.); polystyrenes; polyacrylamides; copolymers of the above co-polymers with the other polymers; cellulosics (including cottons, and other natural and synthetic fibers), and inorganic materials (including alumina, ceramics, silica, glass, and the like). While non-metallic substrates are preferred because of the potential for unwanted adsorption effects, some metals which can form covalent bonds with anchor molecules to space all or part of the HPMP away from the surface can be used. While noble metals such as gold cannot be used, silicon and some metal oxides such as titanium oxide or aluminum oxide may be employed.

The surface of the substrate may be functionalized in a variety of ways to provide amino or carboxyl functionalization sites for bonding thereto of the spacer arm anchor molecules. For polyolefins, oxidation with chromic acid provides a rapid and simple procedure. Alternatively, other functionalization (e.g., via high pressure reaction with oxalyl chloride, plasma oxidation, or radical induced addition of acrylic acid) may be provided. Halogenated materials (e.g., plastics) may be functionalized by base-catalyzed elimination processes introducing double bonds, followed by subsequent addition of amino-functionalized derivatives. Silicas, aluminas, titanium oxides, ceramics and silicons may be conveniently functionalized with any of a variety of commercially available substituted silanes (e.g., aminopropyltriethoxysilane). Hydroxylic compounds (cellulosic membranes, filters, cottons, etc.) are simple to derivatize via a variety of methods. They can be directly carboxymethylated (e.g., with bromoacetic acid); acylated directly with a protected amino acid (e.g., via dimethylaminopyridine catalyzed carbodi-imide coupling with tBoc-glycine). A particularly advantageous method is reaction with carbonyl diimidazole (or phosgene or triphosgene), followed by reaction with a diamine or monoprotected diamine to introduce amino functionalization via a highly stable urethane linkage.

The HPMP matrix material may be any biocompatible, substantially uncrosslinked, high molecular weight, highly soluble polysaccharide, $[S]_n$. Particularly useful are commercially available high molecular weight dextrans (e.g., Pharmacia Dextran T500), although a variety of other polysaccharides (e.g., carrageenans, and guaiac acid derivatives) are suitable alternatives. Carboxymethyl- or amino-functionalized polysaccharides such as cellulose are also suitable.

The degree of functionalization, expressed as functional groups (FGs) per saccharride unit, [S] ranges from about 1:1 $FG:[S]_x$, to about 1:100 $FG:[S]_x$, i.e., x ranges from 1 to 100 per functional group. The molecular weight, MW, of the HPMP polymer may range from about 10K (10,000) to about 10 MM (10 million), with an average around 2 MM, where the polymeric unit is a saccharide. For the typical polysaccharide HPMP of this invention $[S]_n$, n ranges from about 500 to 50K. As noted below, the HPMP strand is anchored in plural places to the substrate surface, SU. In the anchored, folded or convoluted condition, the HPMP forms a thin film layer on the order of about 1000 Å thick (100 nm), where $[S]_1=1$ nm$=10$ Å. Of course, other polymers will have somewhat different lengths. The HPMP must have substantially no crosslinks in order to maintain the matrix flexible, open and freely permeable to the TTMs.

The attachment of the display matrix polymer strand to the substrate surface may be performed by a variety of procedures. It is important that the attachment chemistry functions efficiently in aqueous media to form highly stable chemical bonds. Single point attachment of an HPMP, such as a dextran, to amino-functionalized surfaces is obtained by reductive amination in the presence of sodium cyanoborohydride, of the reducing end of the sugar to an amino functionalized anchor. Alternately, there may be direct attachment to an amino-functionalized substrate surface. This method gives a low anchor density, i.e., number of anchors per $cm^2$ of substrate surface. We prefer methods which form a plurality of attachment points (e.g., 0.001% to 25% of available substrate surface functionalized sites) that are stable during synthesis of ligands and subsequent probings. Stable stapling is needed so that what little glycosidic bond hydrolysis that may occur between the HPMP and the spacer arm, happens only during the more drastic chemical treatments involved in subsequent synthesis of ligands (e.g., piperidine in DMF, trifluoroacetic acid+ethane dithiol+ thioanisole) or during displacements of TTMs, so that little or none of a displayed ligand library will be lost.

The most preferred attachment of the HPMP to the substrate surface involves functionalizing the surface with spacer arm anchor molecules and reacting them with the HPMP by amide bonds. This process is termed "stapling". If the surface bears pendant functional carboxyl groups, e.g., terminal carboxyls on anchor molecules, these must be coupled to amino-functionalized HPMP's, e.g., aminated polysaccharides, by aminating the HPMP before ligand tethering. Both the stapling linkage and tether linkage functional groups can be provided simultaneously by aminating the HPMP with sufficient amino groups for both anchoring and for tethers for ligand attachment. Conversely, if the support surface bears pendant amino groups (on the surface itself or on terminals of anchors) then attachment is achieved by coupling to carboxyl functionalized HPMPs, e.g., carboxymethyl polysaccharides. Unreacted carboxyl groups are then reactivated and coupled to mono-protected bisamines to provide display sites for the ligands.

In another variation, both the masked amino and carboxyl functional groups are incorporated on the polysaccharide. Then, base treatment liberates carboxyl groups for attachment, directly or indirectly, to amino functionalized substrate surfaces or ligands. Alternatively, acid treatment liberates amino groups on the HPMP for attachment to surfaces or ligands that are directly or indirectly carboxyl functionalized.

The chemistry used for polysaccharide-type HPMP coupling (stapling and tethering) is essentially the same, either pre-forming active ester derivatives with carbodiimide reagents, and then adding the amino component, or preforming activated species in the presence of both amino and carboxy-components.

Any particular attachment can be "tuned", that is the amount degree or density of anchors stapling the HPMP to the substrate surface can be controlled, as well as the quantity, degree or level of functionalization of the surface. Thus it is possible to produce different proportions of polysaccharide to surface attachment points (stapling) compared to the loading (concentrating) ligand/library display sites. The Detailed Description below gives Examples of carboxy and amino substituted dextran-type HPMPs at different levels of substitution, and different relative attachment levels.

The use of spacer arm anchor molecules is preferred over direct stapling of the HPMP to the substrate surface. The spacer arms facilitate stapling of the HPMP to the surface and, as noted above, permits control of anchor density (degree of stapling). Where spacer arm anchors are used, the spacer arm is covalently bonded adjacent one end to the surface, as distinct from mere coordination or adsorption to the surface, and the HPMP is covalently bonded adjacent the other end of the anchor molecule. A typical spacer arm molecule spaces the HPMP matrix layer from about 15 to about 50 Å from the substrate surface. A typical spacer may be any biocompatible bifunctionalizable molecule that permits quantitative control of attachment density to the substrate. Examples of alternative spacers include: $C_2$–$C30$ alkanes, polyethers and combinations thereof, such as $C_2$–$C_{30}$ α, ω diaminoalkanes, e.g. 1,3-diaminopropane and 1,6-diaminohexane; a variety of peptides (e.g., oligomers of beta-alanine, aminocaproic acid); polyglycol type derivatives (such as Jeffamine ED-600 from Texaco, O,O'-Bis (2-aminopropyl)-polyethylene glycol 500; and 2,2'-(ethylenedioxy)-diethylamine from Fluka). The presently preferred spacer is Jeffamine ED-600. A typical density is $10^{16}$ anchors/cm$^2$ surface area, but may range from about $10^9$ to about $10^{22}$ anchors/cm$^2$.

As noted, it is important that there be substantially no intra-HPMP crosslinks. The ligands are $MER_n$ molecules having potential affinity binding capability to selected targets, where n of the ligand polymer (MER from polymer) is in the range of from 2 to about 100 constructed assembled monomeric units, such as polypeptides assembled from AminoAcids (AAs). Typical ligands employed in the system of this invention are $MER_n$ ligand libraries including polymers having MER-MER links of the following types: amide; urethane; sulfonamid; thol; thioether; ester; acrylic; and substituted amino (CONX) links. To minimize steric hindrance and promote affinity binding, the ligands are tethered to the HPMP through a single-permanent strong covalent bond so that later displacement of the mating affinity-bound TTM does not sever (hydrolyze) the ligand from the HPMP.

The significance of covalent tethering should not be underestimated. This permits the ligand library to be used repeatedly, i.e., cycled repeatedly through the same or different analyses. The bound libraries of this invention are not destroyed or sacrificed with each affinity screening or probe analysis. The HPMP bound ligand libraries of this invention can be readied for reassay by displacing a prior assay TTM by washing, e.g., with 0.1M acid or alkali, or with 6M urea, concentrated guanidine HCl, a denaturing agent or the like. The library is then ready for another assay, since these TTM displacement procedures do not sever the ligand/tether bond. Since labeled TTMs are used, it is easy to check that the prior assay TTMs have all been removed.

Examples of alternative tethers include: $C_2$–$C_{30}$ alkanes, polyethers and combinations thereof, such as $C_2$–$C_{30}$ α, ω diaminoalkanes, e.g. 1,3-diaminopropane and 1,6-diaminohexane; a variety of peptides (e.g., oligomers of beta-alanine, aminocaproic acid); polyglycol type derivatives (such as Jeffamine ED-600 from Texaco, O,O'-Bis (2-aminopropyl)-polyethylene glycol 500; and 2,2'-(ethylenedioxy)-diethylamine from Fluka). The presently preferred tether is 1,3-diaminopropane.

It should be noted that the anchors and tethers may be identical. Multi-functionalizing the HPMP followed by using some of the functional groups for anchoring and some for tethering, is one preferred approach. Thus, the HPMP can be functionalized with amino or carboxyl groups, or both (i.e., bi-functionalized) and a common anchor/tether molecule, e.g., 1,6-diaminohexane, coupled to the HPMP to form "linker" HPMP. The linker HPMP is then stapled to the surface via only some of the linkers, and the ligands attached on the remaining linkers, or vice versa, via appropriate masking and reaction steps outlined above.

The nature of the HPMP layer as a hydrophyllic thin film is very important, since many ligands displayed as part of libaries may have rapid dissociation of rates from their targets. The thin film (a few 100's of Å to a few 1000's of Å) permits rapid diffusion of an unbound TTM to the bulk solvent outside the matrix before weakly bound TTM's dissociate from their ligands. Thus, fast excess TTM removal procedures compatible with the thin matrix layer of this invention permit hitherto unobtainable screening assays of fast offrate interactions.

The resulting surface-stapled HPMP layer is easily and totally wettable. A preferred surface material is polyethylene, in the form of a thin (ca. ⅛" thick) disc (ca. diameter ¼") called a wink. The HPMP layer is totally transparent, and the HPMP layered wink exhibits a wet sheen or reflectance, as distinct from the duller plastic surface of the bare wink. When immersed in aqueous solution the HPMP layered wink becomes translucent.

Other important uses for HPMP matrices of this invention include coating plates used in ELISA assays, with covalent attachment to the matrix; for implanting immunogenic peptides to raise antibodies for application in immunotherapy, and for raising antibodies needed in basic immunology research. The latter methods would be superior to present methods, which use conjugation to diphtheria toxins and other adjuvants which cause unpleasant side-effects in humans and animals.

DETAILED DESCRIPTION OF THE BEST MODE

The following detailed description illustrates the invention by way of example, not by way of limitation of the principles of the invention. This description will clearly enable one skilled in the art to make and use the invention, and describes several embodiments, adaptations, variations, alternatives and uses of the invention, including what we presently believe is the best mode of carrying out the invention.

Figure 1:
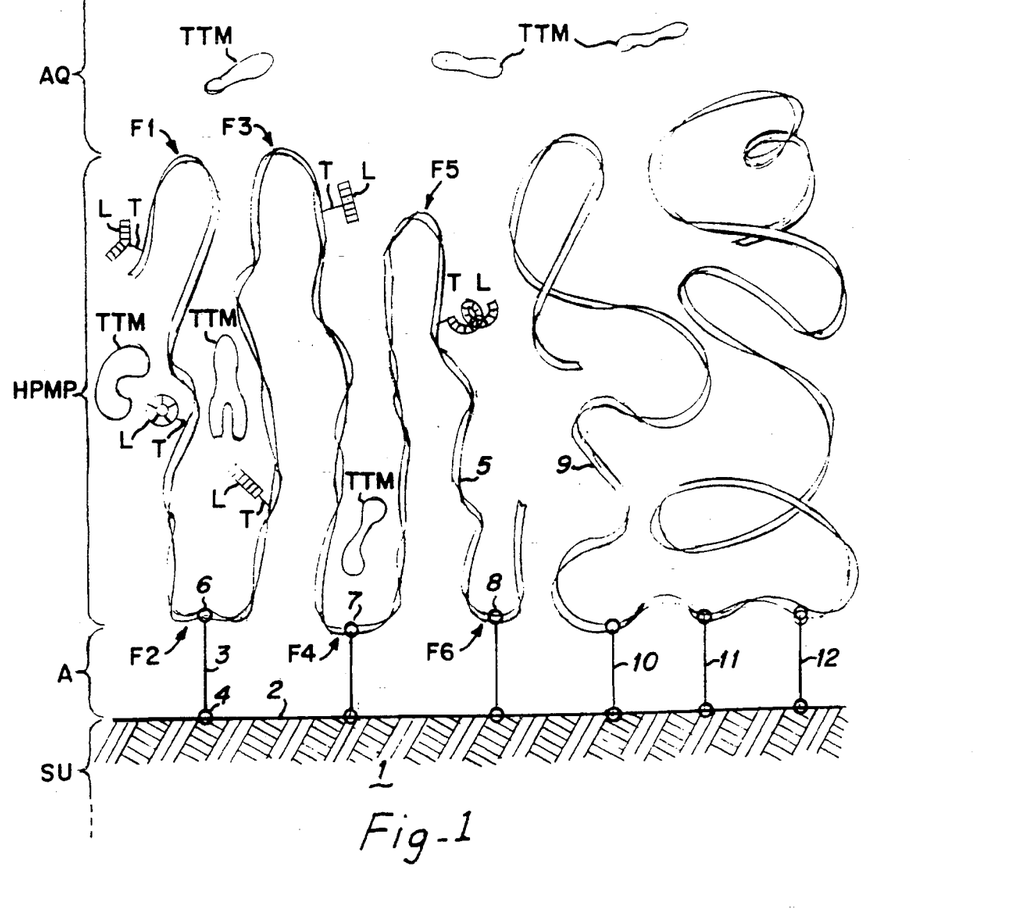
FIG. 1 is a highly enlarged, schematic vertical elevation of the HPMP matrix layer of this invention stapled to a surface, having various mono-tethered ligands and showing free access by TTM's.

FIG. 1 is a schematic, highly magnified vertical cross section of the HPMP matrix substrate system of this invention. The substrate 1 is identified on the left as SU. The surface 2 in this example is functionalized, and spacer arm molecules 3 are covalently bonded at 4 to the surface 1. This anchor layer is designated as A on the left. The spacer arm anchors 3 are also covalently bound to the HPMP strand 5 in a plurality of places 6, 7, 8. The left hand strand is shown folded in a plurality of folds F1–F6 as shown. The right hand strand 9, shown for clarity without ligands bonded by tethers is shown convoluted, with anchors 10, 11, 12 more closely spaced in a medial portion of the polymer chain. The precise configuration is relatively intertwined, but the net result is to create an open matrix layer, identified as HPMP on the left. Various ligands, L, are tethered, T, to the HPMP chain as shown, and the target molecules, TTM, present in an aqueous solution (identified as AQ on the left) freely permeate the highly hydrated matrix as shown. The vertical height is not to scale in FIG. 1. The anchors are typically of density $10^{16}$ anchors/cm$^2$, of length about 15–50 Å, and the fully hydrated height of the HPMP matrix layer is on the order of 200–2000 Å, typically about 1000 Å.

The following examples set forth the best mode of the steps of functionalizing a surface, stapling (anchoring) a typical dextran-type HPMP, tethering ligands, contacting with aqueous solution containing TTMs, and screening.

EXAMPLE 1

Figure 2:
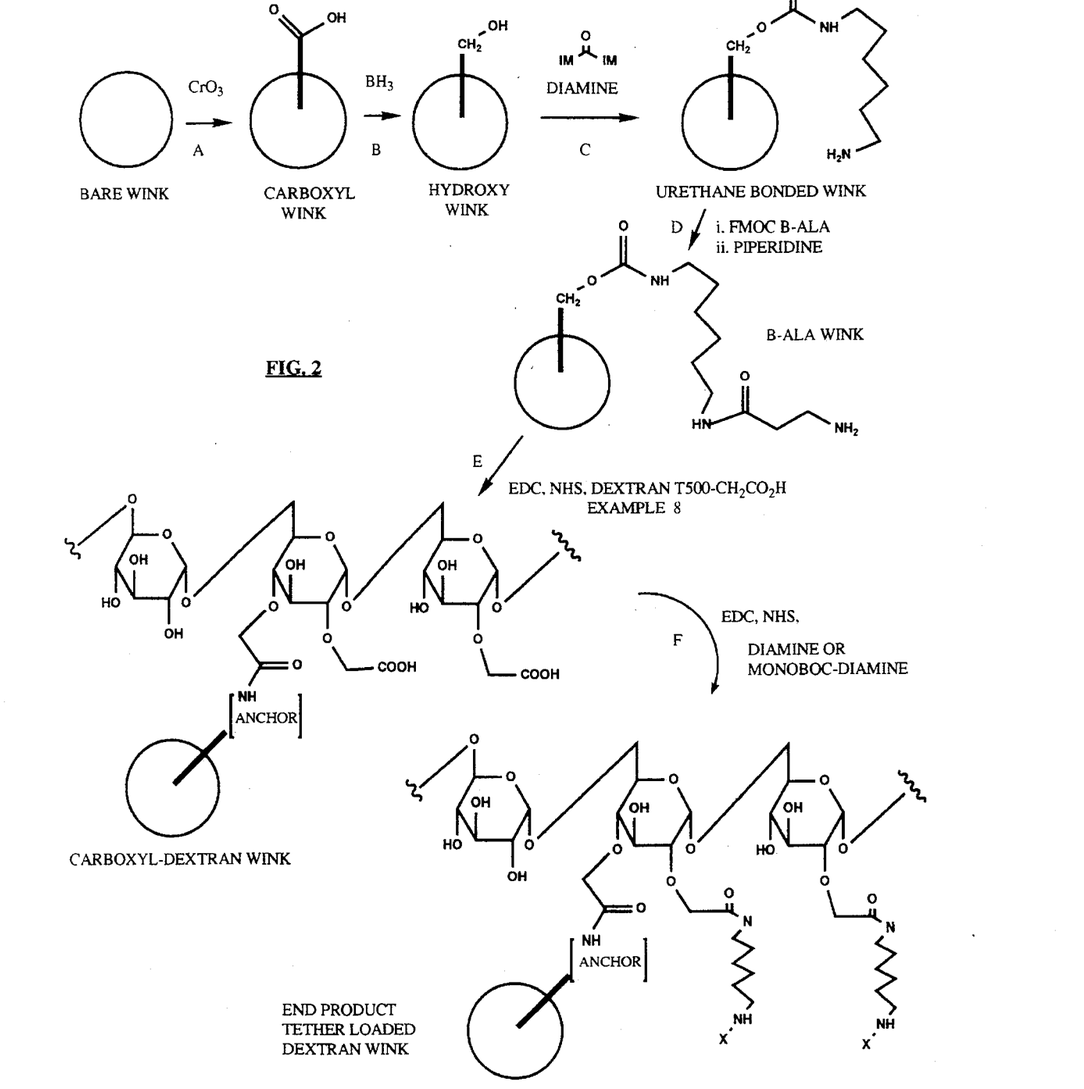
FIG. 2 illustrates a presently preferred method of attachment of the HPMP polymer via carboxyl activation and covalent bonding to amino-functionalized substrate surfaces.

Oxidation of Polyethylene (FIG. 2, Step A)

Polyethylene discs (0.125" thick×0.25" diameter) of the type used in the above-mentioned PILOT process as described in our co-pending Ser. No. 07/939,065 were stirred at 70° C. for 3 hours in chromium trioxide (2.8 g), water (5 mL) and concentrated (herein c.) $H_2SO_4$ (1.55 mL). The discs were washed with water, and dried overnight in vacuo, resulting in the carboxyl wink of FIG. 2.

EXAMPLE 2

Conversion to Acid Chloride

The above discs were placed in a round bottomed flask under nitrogen and stirred with ethanol free chloroform (8 mL) and thionyl chloride (2 mL). After 1 hour the discs were washed with several portions of chloroform (20 mL) and dried in vacuo. This acid chloride functionalized wink is shown on the upper left in FIG. 4.

The following examples 3a, 3b, 4 and 5 show a variety of embodiments of terminal amino-functionalized anchors covalently bonded to discs as substrates.

EXAMPLE 3

Figure 4:
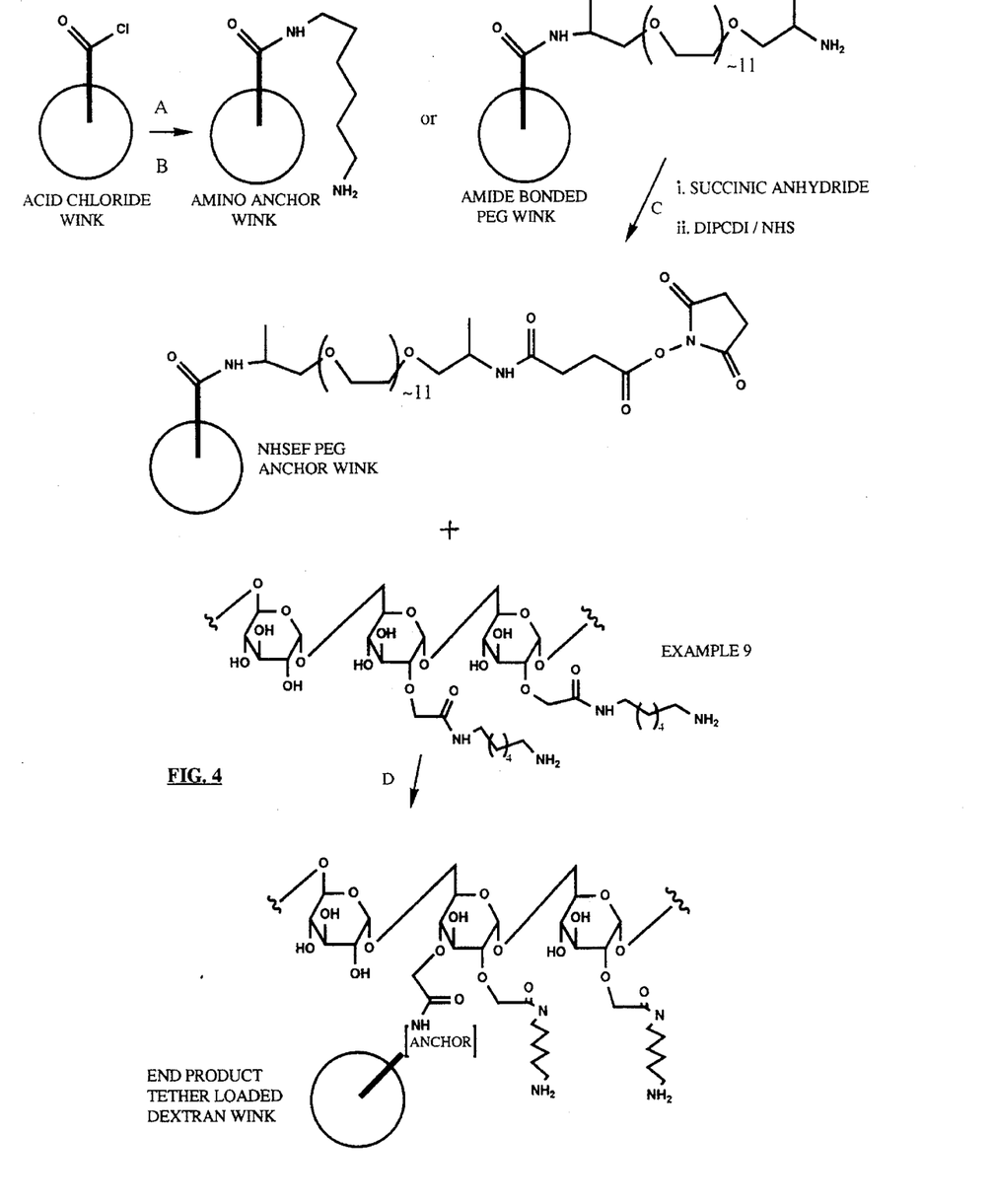
FIG. 4 illustrates a second, converse method of attachment of the HPMP, having amino-functionalized groups, by addition to an activated carboxyl substrate surface.

Conversion of Acid Chloride to Amino-functionalization. (FIG. 4)

a) As shown by step A in FIG. 4, a first sample of 15 acid chloride discs were added to 1,6-diaminohexane (1 g) in methylene chloride (10 mL). The mixture was shaken overnight, then washed with DMF and methanol. Ninhydrin and Fmoc-loading assays show high amino functionalization of the resulting amino anchor wink.

b) As shown in step B of FIG. 4, another sample of the acid chloride discs were treated with polyethylene glycol 500 diamine (Jeffamine ED 600) as above giving similar loading of the resulting amide-bonded PEG wink shown in FIG. 4.

c) As shown schematically in FIG. 4, step C, a sample of 15 PEG amino-functionalized polyethylene discs as prepared in Example 3 (b) were treated with succinic anhydride (0.5 g), 1-hydroxybenzotriazole (0.3 g) and 4,4-dimethylaminopyridine (12 mg) in DMF (10 mL). The reaction was warmed to 60° C. and shaken overnight. The mixture was again warmed, shaken for 1 hour, then washed with DMF, methanol and DMF. Seven of these discs were washed with 1:1 DCM/DMF, then suspended in this mixture (2 mL) and treated with hydroxysuccinimide (NHS, 230 mg) and di-isopropylcarbodiimide (DIPCDI, 0.32 mL). The reaction mixture was shaken overnight, after which the discs were washed with acetonitrile resulting in the NHS ester functionalized (NHSEF) wink as shown in the lower half of FIG. 4, in an unblocked condition. The amino groups may be all or partially blocked.

EXAMPLE 4

Introduction of Amino-functionalization via Urethane. (FIG. 2)

Another sample of several oxidized polyethylene discs were placed in a round bottomed flask equipped with a reflux condenser and stirred at 60° C. in THF (10 mL) and 1M borane in THF (20 mL), step B in FIG. 2. Stirring was continued overnight, by which time reduction to alcohol was complete. The reaction was quenched with water, and the discs washed with water (3×), 1M HCl for 15 minutes, water (3×), and then methanol (3×). The discs were dried in vacuo overnight, then treated with 3 grams of carbonyl diimidazole in 30 mL of DMF (step C in FIG. 2). Vacuum was applied to the apparatus to degas the solution. After 3 hours, the discs were quickly washed with DMF 3× and added to diaminohexane (6.5 g) in methylene chloride (35 mL). Again the mixture was degassed several times, and then stirred overnight. The resulting urethane bonded amino functionalized winks were washed with DMF (5×).

EXAMPLE 5

Addition of Beta-alanine. (FIG. 2,continued)

Fmoc-beta-alanine (1.86 g), PyBOP (2.72 g), HOBt (0.8 g) dissolved in DMF (20 mL) was activated by the addition of N-methylmorpholine (0.7 mL) and added to the amino functionalized winks of Example 4, (see step D of FIG. 2). Vacuum was applied twice to degas the mixture, which was shaken overnight, treated with 20% piperidine in DMF for 20 minutes and washed with DMF (5×) and methanol (5×) and dried resulting in the βAla wink of FIG. 2.

The following two examples (6 and 7) show preparation of a typical HPMP before anchoring to a substrate.

EXAMPLE 6

Low Carboxymethylated Dextran 1 g Dextran T500 (Pharmacia), bromoacetic acid (0.772 g), water (5 mL) and 2M NaOH (5.6 mL) were vortexed and sonicated to form a clear viscous solution. This was left for 20 hours. 1N HCl was added to give pH 3, and then 2 volumes of methanol added. A sticky white solid precipitated and was collected by decanting the supernatant. The precipitation was repeated and finally dialysed against water several times to give, on lyophilization, the product as a very low density white solid having the appearance of a soft spongy mass which is easily separable into filamentary segments. $^1$H NMR shows ca. 1 carboxymethyl group per 4 sugars, considered a low degree of carboxymethylation.

EXAMPLE 7

High Carboxymethylated Dextran 5 g Dextran T500 (Pharmacia),and NaOH (8 g) were dissolved in water (50 mL), and bromoacetic acid (14.5 grams) was added. The mixture was shaken overnight. A further 13.2 g bromoacetic acid and 16 grams of 50% NaOH solution were added and the mixture shaken for a further 24 hours. 6M HCl (ca. 40 mL) was added to bring to pH 2, then the mixture was poured into 300 mL of methanol. The product separates as a white mass of the character described above. A further 150 mL of methanol was added to complete precipitation. The precipitate was dissolved in water, placed in dialysis tubes, and dialyzed against 4 changes of water. The product was obtained by lyophilization as a white powder. $^1$H NMR shows ca. 1 carboxyl group per sugar.

EXAMPLE 8

HPMP (Dextranized) Polyethylene Substrate Surface. (FIG. 2, steps E and F)

Method A: As outlined in FIG. 2, low carboxymethylated dextran of Example 6 (2 g) and hydroxysuccinimide (NHS, 1 g) were treated with water soluble carbodiimide (EDC, 1.5 g) and the pH adjusted to 5 with 2N HCl. The beta-alanine discs produced in Example 5 were added, and the pH adjusted to 8 with 3.5 mL of 2M NaOH. The mixture was stirred overnight giving a gel like mixture. 1M NaOH (10 mL) was added and stirring continued for 35 minutes, to give a clear solution. Discs (also known as "winks") were washed with water (3×) and DMF (5×), resulting in the carboxyl dextran wink of FIG. 2. Excess amino-groups were capped by acetylation with 0.3M acetic anhydride in DMF (20 mL) containing 0.03M dimethylaminopyridine. The winks were washed with DMF and methanol. As shown in step F of FIG. 2, a sample of eighty of these winks were suspended in water (10 mL), and hydroxysuccinimide (NHS, 0.4 g) and EDC (water soluble carbodiimide, 0.6 grams) added. The mixture was sonicated and shaken for 15 minutes. A 3.5M solution of diaminopropane adjusted to pH 9 with c. HCl (2 mL) was added. The reaction was stirred overnight. A further 0.4 mL of the diaminopropane solution was added, and after a further 1 hour, the winks washed thoroughly with water, and DMF, resulting in the end product tether loaded dextran wink shown at the bottom of FIG. 2.

EXAMPLE 9

Amino-functionalized Dextran

The high carboxymethyl substituted dextran of Example 7 (0.36 g) was dissolved in water (5 mL) along with hydroxysuccinimide (NHS, 0.28 g) and water soluble carbodiimide (EDC, 1.31 g). The pH was adjusted to 5 with 2N HCl (50 µL). After 15 minutes tBoc-1, 6-diaminohexane (0.52 g) was added, then 5 mL of water (pH of reaction=8). After shaking at room temp for 30 minutes, the pH had fallen to 7. 2N NaOH (200 µL) was added, and the reaction shaken overnight. The product was dialyzed repeatedly against water, and lyophilized. Since this material had very low water solubility, it was not characterized further, but treated directly with trifluoroacetic acid (10 mL). Rapid carbon dioxide evolution was observed, after 30 minutes anhydrous ether was added (70 mL), and the precipitated product collected by filtration, washed with ether, dried, redissolved in water and lyophilized. The product was now highly water soluble and NMR studies showed ca. 1 amino group per 2 sugar rings. This product was supplied for use in Example 10 (as shown in the lower half of FIG. 4).

EXAMPLE 10

HPMP (Dextranized) Polyethylene Substrate Surface. (FIG. 4)

Method B: A solution of the aminodextran from Example 9 was added to NHSEF winks of Example 3 (c). The amino dextran solution was 150 mg in 1 mL water, with the pH adjusted to 7. The mixture was sonicated then shaken for several days. The discs were washed with water, then methanol, and then dried to give a substrate surface having an HPMP matrix layer with a tether amino substitution of 75 nanomoles. This end product is shown at the bottom of FIG. 4.

EXAMPLE 11

Coupling via 2-Stage Reductive Amination Procedure to Produce Thiol Substituted Dextran Dextran T500 (15 g) was dissolved in water (100 mL), NaCl (15 g) added, then cysteamine hydrochloride (5.5 g). The mixture was agitated vigorously to effect dissolution, then 15M NaOH solution added to bring the pH to 9, and finally sodium cyanoborohydride (5 g) added. The extremely viscous solution was mixed at 70° C. for 2 days. The solution was then cooled to room temperature, placed in a dialysis bag, and dialyzed against several changes of water. The solution was then treated with mercaptoethanol (10 mL) and the pH adjusted to 8. After 2 hours the material was repeatedly dialyzed against water; then lyophilized to give mono-thiol-substituted dextran. Amino substituted polyethylene discs (Example 3a) were treated in DMF at 0° C. with bromoacetic acid (0.14 g), pyridine (0.05 mL) and dicyclohexylcarbodiimide (DCCI, 0.103 g). After 1 hour reaction at room temperature, the bromoacetylated surfaces were washed with DMF to produce bromoacetylated winks. The thioated dextran solution (100 mg in 1 mL water), was treated with sodium borohydride (10 mg for 1 hour) to reduce disulfide bridges. The excess borohydride was destroyed by treating with acetone—2 drops added, pH adjusted to 4, left 10 minutes, and the pH then readjusted to 7. Then the bromoacetylated winks were added to this thioated dextran solution. After shaking for 1 day the discs were washed with water, methanol, and dried to produce end product thio-anchored dextran winks (not tether loaded).

EXAMPLE 12

Production of Dextrans containing Masking Functional Groups. (FIG. 3)

This method allows precise control of loading of tethers for attaching ligands. High carboxymethyl dextran (Example 7, 0.36 g) was dissolved in water (7 mL) and treated with hydroxysuccinimide (0.28 g) and EDC (0.31 g). The pH was adjusted to 5. After mixing for 15 minutes, a solution of tBoc-1,3-diaminopropane (0.28 g, 2 equivs.) and aminocaproic acid methyl ester hydrochloride (0.14 g, 1 equiv) in water (2 mL). After 5 minutes an additional equal volume of 2N NaOH was added to maintain pH. The reaction was shaken overnight, then dialyzed repeatedly and lyophilized to give the diprotected product. NMR studies show incorporation of the 2 functional groups in the correct ratios. This masked bi-functional dextran (MBD) product is shown at the top of FIG. 3. As shown in step A, MBD dextran product was treated with 1N NaOH (10 mL) for 1 hour, the pH adjusted to 3, and dialyzed and lyophilized as above described to give an amino-masked carboxyl HPMP dextran (AMCD) derivative, as shown by NMR.

Figure 3:
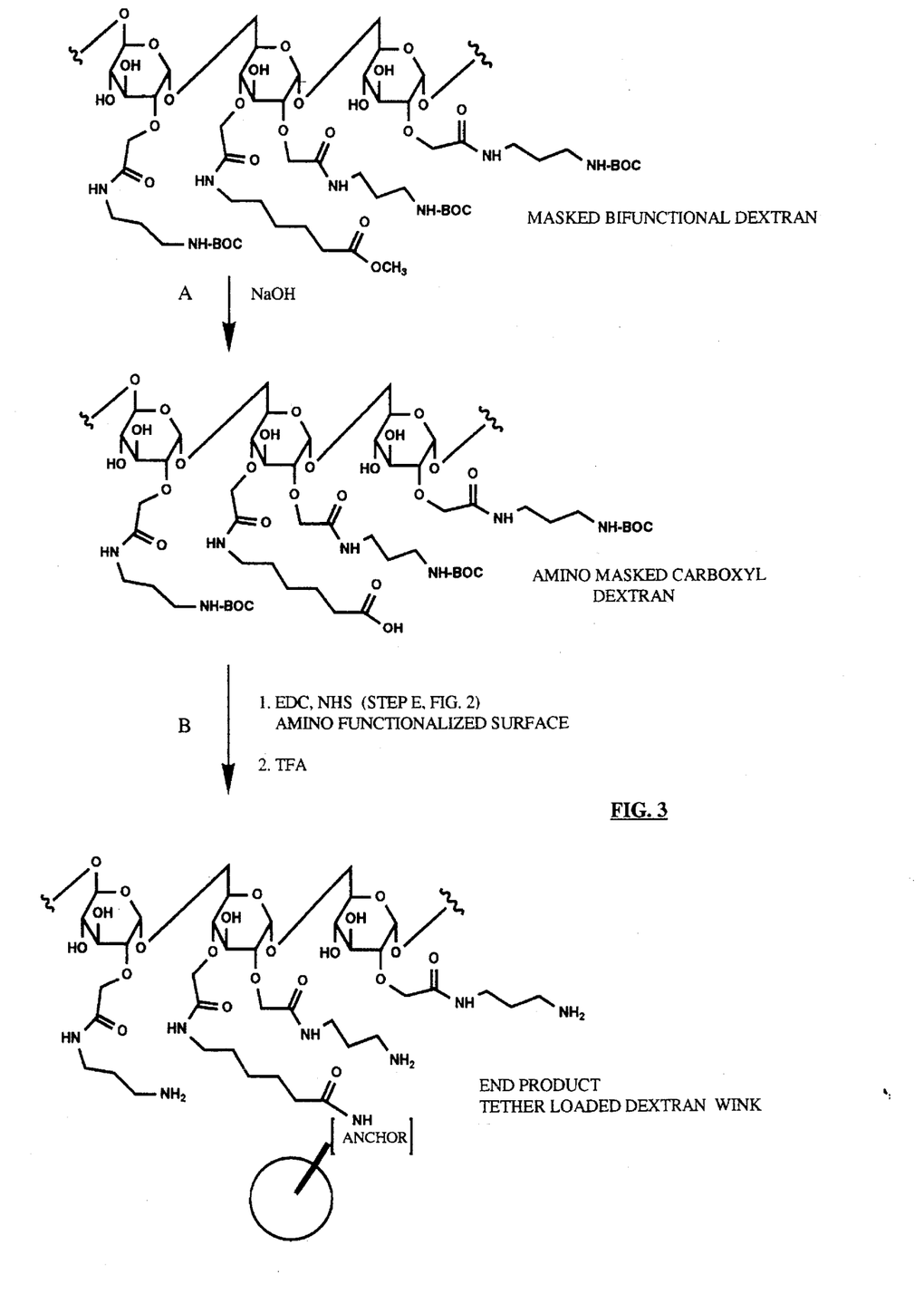
FIG. 3 illustrates a first variation of the attachment method of FIG. 2 in which masked functional groups are incorporated into the HPMP.

As shown in step B of FIG. 3 this AMCD HPMP was coupled to amino-functionalized PE disc surfaces by the process of step E of FIG. 2 described in Example 8. Subsequent TFA treatment then liberated amino sites for library synthesis. The end product tether loaded dextran wink variation is shown at the bottom of FIG. 3.

EXAMPLE 13

Comparative Test—TFA Stability of Stapled Dextranized Surfaces Compared to Epichlorohydrin Bonding Winks were dextranized in accord with the above Examples 8 and 10 (Sample A). By way of comparative tests, dextran was bonded to polyethylene surfaces using epichlorohydrin (Sample B), as used by Pharmacia Biosensor AB in connection with the BIAcore$_{tm}$ surface plasmon resonance biosensor systems (see Lofas, S. and Johnsson, B., A Novel Hydrogel Matrix on Gold Surfaces in Surface Plasmon Resonance Sensors for Fast and Efficient Covalent Immobilization of Ligands, J. Chem. Soc. Chem. Commun. 1990 pp. 1526–1528; also see WO 92/06380, WO 90/05295 and WO 90/05305). Both samples were treated with TFA for various time intervals up to 2 hours. The samples were then analyzed by quantitative sugar loading assays. After only 2 hours, around 90% of dextrans were lost from the epichlorohydrin bonded surfaces, whereas only minor loss (<10%) was detected from the wink surfaces stapled according to the processes of this invention.

EXAMPLE 14

Peptide Synthesis on HPMP

Figure 5:
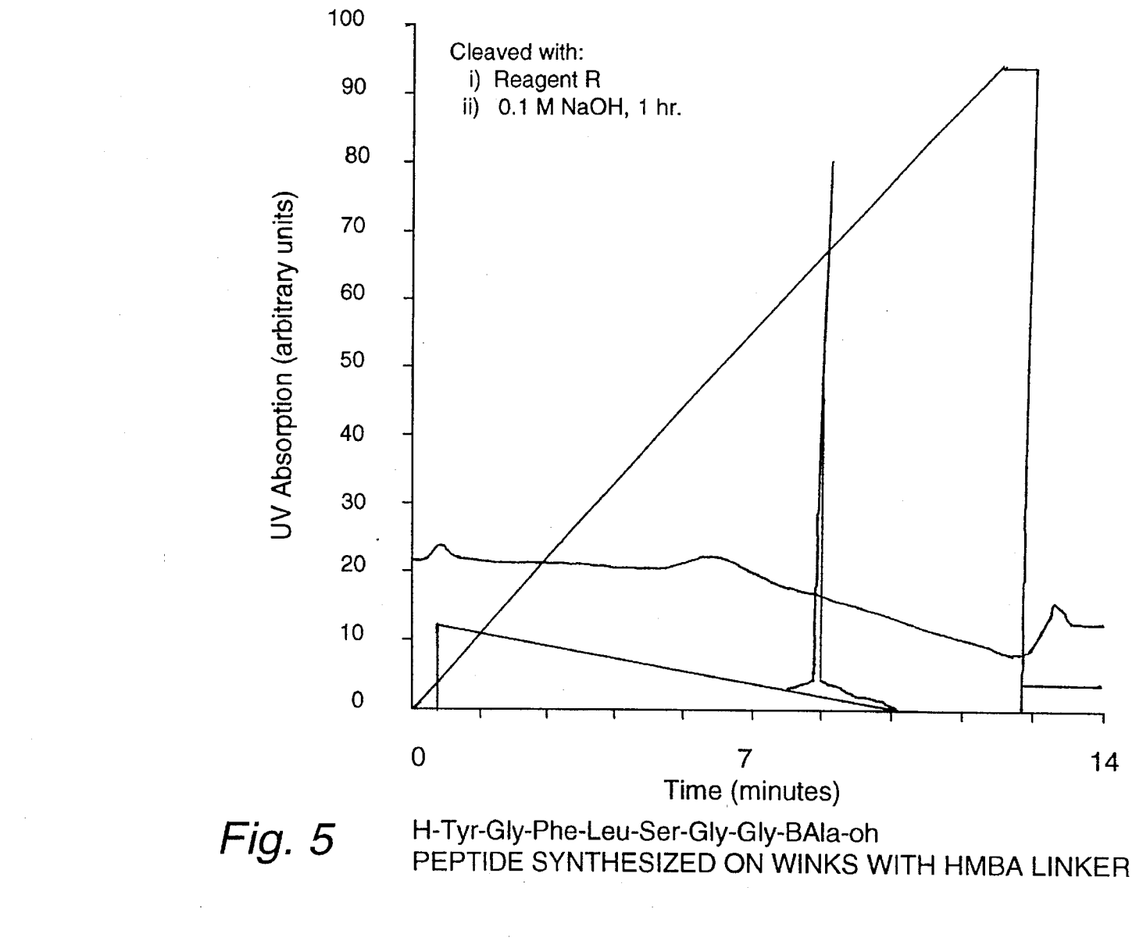
FIG. 5 is an HPLC chromatogram of removal of an endorphin octapeptide assembled on an HPMP wink of this invention.

A variety of peptide sequences were assembled on tether loaded HPMP wink surfaces in accord with the invention. FIG. 5 shows assembly of the octapeptide YGGFLSGG-βAla, the epitope of the 3E7 antibody, on stapled dextran winks of Example 8. A hydroxymethylbenzoic acid cleavable linker was first added to the tether, and then the peptide chain assembled by an automated peptide synthesizer (Millipore) by conventional peptide synthesis chemistry. The peptide was treated with reagent R, a standardized TFA cocktail, to remove side chain protective groups, and then cleaved with 0.1M NaOH for 1 hour. The HPLC chromatogram of FIG. 5 shows the resulting extremely sharp elution peak at 8.75 minutes, which demonstrates recovery of highly pure peptide after cleaving. This establishes covalent linkage for display via the tether on the HPMP dextran, and that ligand assembly had successfully occurred in situ on the HPMP. The relative purity of the recovered peptide shows the assembly sequencing was synchronous and complete at all the sites on the HPMP. Additional experimental work established the use of other cleavable linkers, such as the PAL linker (Millipore) which was cleaved with TFA.

EXAMPLE 15

Signal to Noise Ratio

Amino-functionalized tether-loaded winks of Example 8 had the ligand HPQFVSGG-βAla (herein HPQ) assembled thereon by the process as in Example 14. This ligand exhibits weak binding with Streptavidin, in that micromolar quantities need be present for binding to be detected as compared to the strong binding of YGGFLSGG-βAla of Example 14 in which only nanomolar quantities need be present to exhibit uptake of 3E7 anti-endorphin monoclonal antibody.

The peptide loading of the winks was 50 nmoles/wink. The winks were suspended in 150 μL of phosphate buffered saline, and various concentrations of $^{125}$I-radiolabeled Streptavidin were added and incubated for ca. 2 hours. The winks were washed and counted on a gamma counter to determine binding saturation.

TABLE I

| | HPQ Winks Uptake | |
|---|---|---|
| TEST | Amount $^{125}$I-Streptavidin | Counts per Minute × 10$^6$ |
| 1 | 10 μL | .32–.5 |
| 2a | 10 μL + 10-fold cold | .32* |
| 2b | 100 μL | 3.2 |
| 3 | 100 μL + 10-fold cold | 2.1–2.8* |
| 4 | 100 μL + 100-fold cold | .69** |

*Multiply by 10 for conversion to 10-fold cold corrected counts.
**Multiply by 100 for conversion to 100-fold cold corrected counts.

10 μL of $^{125}$I-Streptavidin exhibits 750,000 cpm and equals 0.1 μg, about 1.6 pM Streptavidin. Test #1 shows a range for several runs (5) of 320,000 to 500,000 counts per minute, an excellent uptake in the range of 42–67%.

Standard practice is to use non-radiolabeled Streptavidin, called "cold" solution, to dilute the radiolabeled sample. This permits higher concentrations to be assayed without massive amounts of radioactive material being employed. Thus, Tests 2a and 2b can be directly compared, 2b being a full concentration radiolabeled sample. Since the 2b counts are equivalent to the dilution multiple counts of 2a, the cold dilution sample 2a multiplied by the 10-fold factor is accurately representative of a non-diluted test. That is, Test 2a/2b confirms the validity of using the "X-fold cold" multiplying factor for ligands on the HPMP of this invention.

The value of 69×10⁶ cpm in Test 4 corresponds to about 147 pmoles Streptavidin bound to the wink. AA analysis showed 10–20 nmoles of peptide on each wink. This series of tests represents "signal" strength.

A second series of tests of non-ligand-loaded but amino-functionalized (50 nmoles) winks was run to determine background "noise". These non-loaded winks were incubated in a vial of 150 μL of the saline buffer, and 10 μL $^{125}$I-Streptavidin was added and incubated. After incubation the supernatant solution was pipetted off and the winks washed by various techniques. Table II shows the results.

TABLE II

Unloaded Wink Washing

| TEST | Amino-functionalized Non-Ligand-Loaded Winks | CPM Supernatant (Unbound) | Bound to Wink |
|---|---|---|---|
| 5 | Vortex Washing 5x .7 ml buffer | 680,000 | 6,957 |
| 6 | Vacuum Washing 5x .7 ml buffer | 660,000 | 3,824 |
| 7 | Centrifuge 3 min 13k | 690,000 | 10,117 |
| 8 | Vacuum Washing 25 ml | 750,000 | 350 av 3 runs |
| 9 | Vacuum Washing | 7.5 × 10⁶ | 2,100 av 2 runs |

These results show an extremely low background count noise level, which means that even the very large Streptavidin tetramer molecule of 60,000 Daltons MW can be easily washed out of the convoluted HPMP matrix. Thus, the incidence of the Streptavidin becoming caged in the matrix is very low, with the result that false binding is not an appreciable effect. In addition the S/N ratio is very high. In Test 9, for example, the unbound is about 7.5×10⁶ counts; from Test 2b above one would expect 3.2×10⁶ bound. But only 2100 counts were registered which shows the S/N ratio was over 1500 bound/unbound residual in the HPMP matrix.

Test 7 shows that only a thin film of solvent plus solute is tightly bound as a hydration layer for the HPMP, allowing assay of extremely fast offrate interactions. Even in the absence of washing, an equilibrium enrichment of 100:1 of the labeled Streptavidin would be detected.

EXAMPLE 16

Quantitative Sensitivity

The HPQ ligand was assembled as above on tethered dextran HPMP stapled winks of Example 8 but without a cleavable linker, and Reagent R used to remove side chain blockers. Several different loading samples were prepared: one with zero (no HPQ); two at 50 nmoles; and one at 80 nmoles. These HPQ ligands loaded on HPMP tethers were incubated for several hours to progressively increasing amounts of $^{125}$I labeled Streptavidin, as a sample TTM, in buffered saline solution. The winks were removed, vacuum washed in the buffered saline, and the bound Streptavidin counted. Table III shows the data and FIG. 6 graphically shows the results as smoothed curves.

TABLE III

| | HPQ Saturation in CPM × 10⁶ | | | | | | | |
|---|---|---|---|---|---|---|---|---|
| | 50 nmoles ● | | 80 nmoles ▲ | | 50 nmoles △ | | Unloaded ■ | |
| Test # | Bound | Total | Bound | Total | Bound | Total | Bound | Total |
| 10 | 0.500 | 0.775 | 0.042 | 1.140 | 0.013 | 0.650 | 0.000 | 0.500 |
| 11 | 3.200 | 7.750 | 0.775 | 11.690 | 1.260 | 6.700 | 0.001 | 0.650 |
| 12 | 9.800 | 23.250 | 0.719 | 6.456 | 0.559 | 4.520 | 0.002 | 6.250 |
| 13 | 24.500 | 77.500 | 14.392 | 64.160 | 9.919 | 45.200 | 0.005 | 62.500 |
| 14 | 69.000 | 775.000 | 94.361 | 624.800 | 61.052 | 452.000 | 0.005 | 625.000 |

Figure 6:
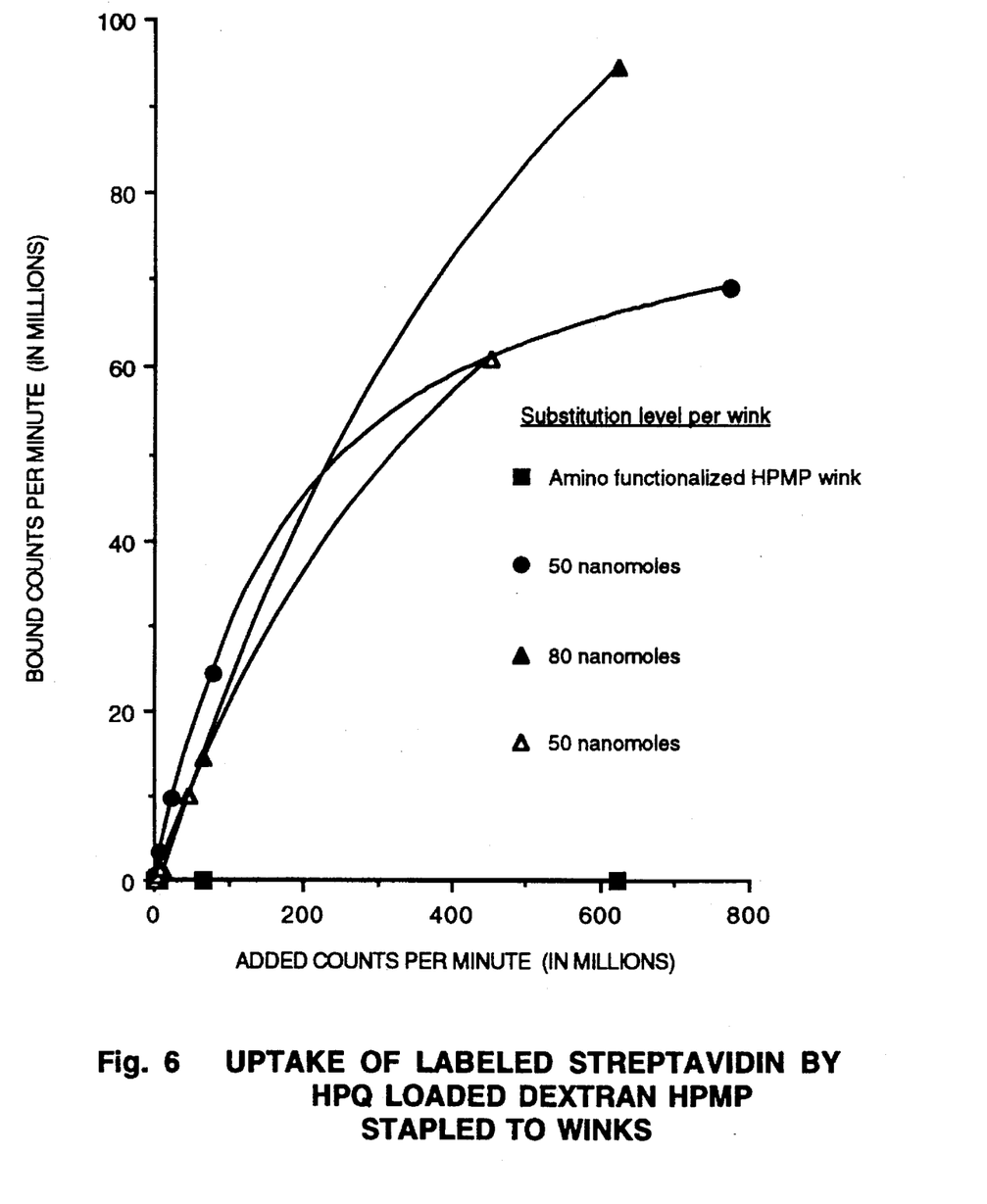
FIG. 6 illustrates the uptake of radioactivity from $^{125}I$ labelled streptavidin on an HPQ ligand (which mimics biotin) using the HPMP system of this invention.

FIG. 6 shows the data in a graph form. The curve of the solid triangle data points represents an 80 nmoles-loaded peptide on the HPMP. The solid circle and triangle are 50 nmoles loadings on two slightly different HPMP lots. The comparison non-loaded amino-functionalized winks are represented by the solid square symbols; they do not even show on the abcissa of the graph, i.e., the background noise curve is essentially flat. The 80 nmoles curve peaks at about 130–140×10⁶ CPM. The results show essentially linear uptake through about 50–80 million CPM. This means that the HPMP system behaves exactly as it would be predicted, had the measurements been carried out with untethered molecules in solution. Also the HPMP system of the invention can be used quantitatively; that is, count readings (intensity) can be quantitatively correlated to amounts of bound TTMs. The high slope and total amount of bound counts indicates high sensitivity of the method.

EXAMPLE 17

Fast Off-Rate Analyses

Over washing can remove specifically bound ligands if these ligands have a fast off-rate. The more extensive the washing the more signal is removed. In cases of fast off-rate TTM/ligand pairs, analysis can be accomplished by simply removing the solution containing the labelled TTM. This can be done by centrifugation to remove unbound TTMs. Samples of HPQ ligand/125-I Streptavidin were assembled as in Example 16 and ligand/125-I Streptavidin were assembled as in Example 16 and subjected to comparative unbound TTM removal Tests 15–17 below. The loadings were 50 nmoles in all three tests.

TABLE IV

COMPARATIVE REMOVAL TESTS

|  | CPM × 10⁶ | |
| --- | --- | --- |
|  | Bound | Total |
| TEST 15 CENTRIFUGATION: 13,000 RPM for 3 MIN. | | |
| HPQ | 0.56 | 0.7 |
| Amino functionalized* | 0.01 | 0.7 |
| TEST 16 VACUUM WASH | | |
| HPQ | 0.35 | 0.7 |
| Amino functionalized* | 0.0038 | 0.7 |
| TEST 17 VORTEX WASH | | |
| HPQ | 0.31 | 0.7 |
| Amino functionalized* | 0.007 | 0.7 |

*No ligand.

As shown by comparing the bound CPM for centrifugal removal vs. vacuum wash and vortex wash, the centrifugation gives higher count for identical loadings. This shows that centrifugation does not remove TTMs specifically bound to ligands, even if the ligand or TTM has a very fast off-rate. The bound counts on non-washed, centrifugation-removed excess TTM represents an assay of the equilibrium enrichment of labelled target bound to the ligand. This centrifugation is the preferred unbound TTM removal method for fast off-rate or weak binding TTM/ligand pairs and permits analysis of such TTMs by the system of this invention It should be understood that various modifications within the scope of this invention can be made by one of ordinary skill in the art without departing from the spirit thereof. For example, the back of the polyethylene PILOT discs (winks) may be coated or protected so that only one side of the discs is functionalized for stapling to the HPMP. In the alternative, two layers of disc film (PE film) may be removably adhesively laminated, discs punched out, treated in accord with the invention to produce double-side stapled HPMP which may include tethers, then peeled apart to form two, one-sided winks. The winks can be porous or solid polyethylene or other plastic. We therefore wish our invention to be defined by the scope of the appended claims as broadly as the prior art will permit, and in view of the specification if need be.

---

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 9
        ( B ) TYPE: Amino Acids
        ( C ) STRANDEDNESS:
        ( D ) TOPOLOGY: Linear     ( i i ) MOLECULE TYPE: Peptide
        ( A ) DESCRIPTION:

( i x ) FEATURE: Exhibits strong binding with 3E7 antibody;
            biological activity not determined, but
            expected to have opiate and related CNS
            activity
        ( A ) NAME/KEY: 3E7 test YGG peptide
        ( B ) LOCATION:
        ( C ) IDENTIFICATION METHOD: Constructed using a
            Millipore Model 9600 peptide synthesizer
        ( D ) OTHER INFORMATION: Leuenkephalin amino terminus is
            YGGFL     ( x ) PUBLICATION INFORMATION:
        ( A ) AUTHORS: Hughes J., Smith T.W., Kossterlitz H.W.,
            Fothergill L.A., Morgan B.A., Morris H.R.
        ( B ) TITLE:
        ( C ) JOURNAL: NATURE
        ( D ) VOLUME: 258
        ( E ) ISSUE:
        ( F ) PAGES: 577-
        ( G ) DATE: --,--, 1975
        ( H ) DOCUMENT NUMBER:
        ( I ) FILING DATE:
        ( J ) PUBLICATION DATE:
        ( K ) RELEVANT RESIDUES IN SEQ ID NO: 1: From 1 to 9

( x i ) SEQUENCE DESCRIPTION: SEQ ID NO: 1:

His    Pro    GLn    Phe    Val    Ser    Gly    Gly    βAla
        1                                      5

( 2 ) INFORMATION FOR SEQ ID NO: 2:

( i ) SEQUENCE CHARACTERISTICS:
      ( A ) LENGTH: 9
      ( B ) TYPE: Amino Acids
      ( C ) STRANDEDNESS:
      ( D ) TOPOLOGY: Linear ( i i ) MOLECULE TYPE: Peptide
      ( A ) DESCRIPTION:

( i x ) FEATURE: Exhibits weak specific binding with
              Streptavidin; biological activity unknown
      ( A ) NAME/KEY: HPQ Sequence Ligand for Streptavidin Test
      ( B ) LOCATION:
      ( C ) IDENTIFICATION METHOD: Constructed using a
              Millipore Model 9600 peptide synthesizer
      ( D ) OTHER INFORMATION: HPQ and HPQFV subparts
              described in Lam et al in Peptide Symposium
              paper.

( x ) PUBLICATION INFORMATION:
      ( A ) AUTHORS: Lam K.S., Salmon S.E., Hersh E.M., Hruby
              V.J., Al- Obeidi F., Kazmierski W.M., Knapp R.J.
      ( B ) TITLE: The selectide process: Rapid generation of
              large synthetic peptide libraries linked to
              identification and structure determination of
              acceptor- binding ligands
      ( C ) JOURNAL: Peptides, Chemistry and Biology;
              Proceedings of the Twelfth American Peptide
              Symposium, J.A. Smith and J.E. Rivier, Eds., Escom,
              Leiden
      ( D ) VOLUME:
      ( E ) ISSUE:
      ( F ) PAGES: 492-495
      ( G ) DATE: --,--, 1992
      ( H ) DOCUMENT NUMBER:
      ( I ) FILING DATE:
      ( J ) PUBLICATION DATE:
      ( K ) RELEVANT RESIDUES IN SEQ ID NO: 2: 1 to 9

( x i ) SEQUENCE DESCRIPTION: SEQ ID NO: 2:

Tyr  Gly  Gly  Phe  Leu  Ser  Gly  Gly  βAla
      1              5

We claim:

1. A ligand display system for highly accessible, flexible three dimensional display of tethered ligands for affinity binding to displacable tagged target molecules which comprises in operative combination:
   a) a biocompatible non-gold substrate having a surface; and
   b) a biocompatible hydrophilic polar multi-functionalized substantially non-crosslinked, long-chain polysaccharide, wherein said long-chain polysaccharide is anchored to said substrate surface by a plurality of covalent bonds at multiple points spaced along the length of said long-chain polysaccharide, wherein said covalent bonds are present in an amount sufficient to minimize loss of polysaccharide chain from said surface upon exposure to trifluoroacetic acid and to minimize the effect of hydrolysis in said long-chain polysaccharide during peptide synthesis deprotection, to form a thin film three dimensional functionalized matrix layer above said substrate, in an open, freely permeable configuration for the covalent tethering of ligands thereon, and for access thereinto of target molecules for affinity binding to preselected ligands.

2. The ligand display system of claim 1 wherein said long-chain polysaccharide is covalently anchored to said substrate by biocompatible spacer arm molecules.

3. The ligand display system of claim 1 wherein said biocompatible non-gold substrate is selected from the group consisting of functionalized plastic, glass, alumina-containing material, silica-containing material, and silicon-containing material.

4. The ligand display system of claim 3 wherein said functionalized plastic is a polyolefin plastic.

5. The ligand display system of claim 4 wherein said polyolefin plastic is porous, and is in the form of a thin disc functionalized for attachment to said long-chain polysaccharide.

6. The ligand display system of claim 1 wherein said long-chain polysaccharide is selected from the group consisting of dextran, carboxymethylcellulose, and guaiac acid, said long-chain polysaccharide having a molecular weight in the range of from about 10,000 to about 10 million.

7. The ligand display system of claim 6 wherein said long-chain polysaccharide includes functional groups, with the number of functional groups per saccharide unit in the range of from 1 functional group per saccharide unit to about 1 functional group per 100 saccharide units.

8. The ligand display system of claim 1 which includes preselected ligands covalently tethered to said long-chain polysaccharide.

9. The ligand display system of claim 8 wherein said preselected ligands are mono-tethered to said long-chain polysaccharide.

10. The ligand display system of claim 8 wherein said ligands are synthesized in situ on said thin film three dimensional functionalized matrix layer.

11. The ligand display system of claim 10 wherein the loading of said preselected ligands on said long-chain polysaccharide ranges from about 1 ligand per saccharide unit to about 1 ligand per 100 saccharide units.

12. A ligand display system as in claim 11 wherein said preselected ligand is a polymer of n monomeric units wherein n ranges from about 2 to about 100 and said monomeric units of the polymer are selected from the group consisting of protected L-, D- and non-natural amino acids and mixtures thereof; and protected DNA monomers and protected RNA monomers and mixtures thereof, wherein said DNA and RNA monomers are natural or unnatural bases.

13. A ligand display system as in claim 12 wherein at least some of said preselected ligands comprise a preselected library of related compounds.

14. A ligand display system as in claim 13 wherein said preselected library is a peptide library.

15. A ligand display system as in claim 8 which includes at least one preselected target molecule affinity bonded to at least one of said preselected ligand molecules.

\* \* \* \* \*